United States Patent
Benedetti

(10) Patent No.: US 6,895,074 B2
(45) Date of Patent: May 17, 2005

(54) NON-DESTRUCTIVE PROCESS FOR CONTINUOUSLY MEASURING THE DENSITY PROFILE OF PANELS

(75) Inventor: Paolo Benedetti, Modena (IT)

(73) Assignee: IMAL Srl (IT)

( * ) Notice: Subject to any disclaimer, the term of this patent is extended or adjusted under 35 U.S.C. 154(b) by 35 days.

(21) Appl. No.: 10/152,087

(22) Filed: May 20, 2002

(65) Prior Publication Data

US 2005/0047545 A1 Mar. 3, 2005

(30) Foreign Application Priority Data

May 18, 2001 (EP) ............................................ 01830321

(51) Int. Cl.⁷ ................................................ G01B 15/02
(52) U.S. Cl. ........................................ 378/89; 378/70
(58) Field of Search ............................. 378/89, 70, 86, 378/87, 88, 90

(56) References Cited

U.S. PATENT DOCUMENTS

| | | | |
|---|---|---|---|
| 2,997,586 A | | 8/1961 | Scherbatskoy |
| 4,228,351 A | | 10/1980 | Snow et al. ................. 250/273 |
| 4,918,712 A | * | 4/1990 | Le Floc'h et al. ............. 378/89 |
| 5,195,116 A | * | 3/1993 | Le Floc'h et al. ............. 378/89 |
| 5,195,117 A | | 3/1993 | Ong ............................. 378/89 |
| 5,548,626 A | * | 8/1996 | Warnecke ...................... 378/54 |
| 5,729,582 A | * | 3/1998 | Ham et al. ..................... 378/89 |
| 5,970,116 A | * | 10/1999 | Dueholm et al. ............. 378/90 |
| 6,094,470 A | * | 7/2000 | Teller ........................... 378/54 |
| 6,563,906 B2 | * | 5/2003 | Hussein et al. ............... 378/89 |

* cited by examiner

*Primary Examiner*—Edward J. Glick
*Assistant Examiner*—Hoon Song
(74) *Attorney, Agent, or Firm*—The Bilicki Law Firm, P.C.

(57) ABSTRACT

A method for nondestructively measuring the density of a panel, comprising the steps of: directing a collimated radiation beam at the panel at an oblique angle; passing the panel under the collimated radiation beam or passing the collimated radiation beam over the panel; continuously detecting a resultant beam of a plurality of photons with a detector directed at the panel; counting only those photons with an energy level above a minimum energy level; correcting for inaccuracies at the edges of the panel; and generating a density profile of the panel throughout the thickness of the panel.

42 Claims, 5 Drawing Sheets

NON-DESTRUCTIVE PROCESS FOR CONTINUOUSLY MEASURING THE DENSITY PROFILE OF PANELS

CROSS-REFERENCE TO RELATED APPLICATIONS

This application claims priority to European patent application number EP 01830321.4, filed on May 18, 2001, which is incorporated herein in its entirety.

FIELD OF INVENTION

The present invention relates to quality control in the production of composite panels, in particular wooden panels. More precisely, the present invention relates to a method for continuously measuring the density profile of composite and other panels.

BACKGROUND OF THE INVENTION

It is well-known that, if the thickness of a material is known, one can determine the average density of a material by using radiation beams that are absorbed by the same material. The absorption is a function of the mass absorption coefficient, A, which depends on the type of material. Therefore, the density is proportional to the attenuation of the radiation, in photons X or γ, through the material and can be measured directly provided the thickness is known and the material is homogeneous.

The "Compton scattering technique" is also known for determining the density of a material. With this technique, the density distribution of a material is examined by passing a collimated beam of photons through the material and analyzing the radiation that is scattered by the same material. This measurement does not depend on the thickness of the material.

As is well known in quantum physics, according to the Compton effect, the trajectory and energy of a photon changes when said photon interacts with an atom. Under the Compton effect, the difference of energy of the photon before the interaction and after the interaction is responsive to the direction of the new photon with respect to the direction of the primary photon. As is known, the energy is inversely proportional to the wavelength, and the variation of wavelength derives from the known Compton equation:

$$\lambda' - \lambda = \frac{h}{mc}(1 - \cos\theta) = \frac{2h}{mc}\sin^2\left(\frac{1}{2}\theta\right).$$

where h is Planck's constant, c is the speed of light, m is the mass of an electron and θ is the angle of diffusion. From this equation, it is clear that it is important to know the energy of the incident photon in order to determine the energy of the photon after the interaction with the detected material at a suitable angle θ. However, it is not easy to know a priori the energy of the incident photon if it is produced by a radiation source, since an X-ray tube emits photons with a very extended spectrum range. In turn, the photon produced under the Compton effect will undergo further interactions within the same material and before it is detected. In particular, it can be attenuated along the chosen direction within a probability range.

SUMMARY OF THE INVENTION

According to the invention, a non-destructive process for continuously measuring the density profile of a panel comprising the steps of:

transmitting a collimated main radiation, wherein said radiation is X or γ radiation, through the material of the panel;

measuring the radiation under Compton effect scattered by a particle of material that is crossed by the main radiation, said measuring being carried out by a detector of photons producing a signal responsive to the energy of the radiation scattered by the particle;

performing spectral analysis of the scattered signal and selection of a signal that is comprised within a predetermined range;

measuring or counting the photons detected after the selection of the spectral analysis in said range; and tracing the density profile by repeating the measure for a discrete succession of particles crossed by the main radiation for all the thickness of the panel.

The spectral analysis comprises a step of discrimination of the photons versus their energy and detection of all those comprised within a suitable range of energy with a predetermined amplitude as a function of the material to analyze.

In one embodiment, the main radiation is incident with an inclination of about 45° with respect the surface of the panel and the scattered radiation is measured at about 90° with respect to the direction of the main radiation.

The step of measuring the scattered radiation is carried out by a photomultiplier with scintillator and with output signal of pulsed type, the scintillator creating a number of photons responsive to the energy of the radiation scattered by the particle and the photomultiplier creating a voltage pulse depending upon the energy of the photons produced by the scintillator, the succession of the voltage pulses measured then undergoes spectral analysis.

In order to scan the panel for all the thickness, the detector is movable for measuring the scattered radiation along the direction of the main radiation, the density profile being given by the series of pulses recorded for each position of the detector.

The measure of the scattered radiation is carried out by collimation of the radiation on the scintillator, for focusing the measure only on a particle of the material, in order to analyse only the photons produced under Compton effect in the particle.

In order to scan the panel at the edges a correction step is provided by means of an algorithm that considers: the thickness of the beam of the main radiation, the angle of the collimator and the geometry of the panel at the side edges.

The scanning of the panel is carried out with panel in movement during the production process, considering the characteristics of the panel constant during the measure.

According to another aspect of the invention, an apparatus for continuously measuring the density profile of a panel comprising:

means for collimated transmission of radiation, wherein said radiation is X or γ radiation, oriented obliquely with respect to one side of the panel;

at least one detector of radiation scattered under Compton effect by a particle of material, said detector being arranged at a predetermined inclination with respect to the means for transmission, means for movement of the at least one detector for scanning the scattered radiation for all the thickness of the panel, means for spectral analysis of the scattered signal and for selection of the signal that is comprised within a predetermined range; and computing means of the signal depending upon the scattered radiation of the material for calculating the density of the particle.

The means for spectral analysis in one embodiment comprise:
  means for the measure of photons;
  means for discrimination of said photons according to their energy;
  means for counting and measuring only the photons that are comprised within a suitable selected range of predetermined amplitude.

In one embodiment, the means for transmission are oriented about 45° with respect the surface of the panel and the at least one detector is oriented at about 90° with respect to the direction of the means for transmission.

The detector comprises a photomultiplier with scintillator and with output signal of pulsed type, the scintillator creating a number of photons responsive to the energy of the radiation scattered by the particle and the photomultiplier creating a voltage pulse depending upon the energy of the photons produced under the scintillator, the succession of the voltage pulses as measured then undergoes spectral analysis.

The detector can be moved parallel to the direction of the main radiation by a carriage driven by a motor on which the detector is located, the motor moving the carriage according to a predetermined speed function and the pulses transmitted by the detector are responsive to the instant position of the motor.

The detector is associated to a collimator that has the object of focusing the detector only on a particle of the material, for measuring only the photons produced under Compton effect in the particle. In one embodiment, the collimator has shape of frustum of pyramid by a high number of metallic blades.

The apparatus is associated to an electronic control unit comprising: the means for spectral analysis, the attenuation computing means, as well as software means of correction for scanning the panel near the side edges.

BRIEF DESCRIPTION OF THE DRAWINGS

Further characteristics of the process and of the apparatus according to the present invention will be made clearer with the following description of an embodiment with reference to the attached drawings, which serve to illustrate but not limit the invention.

DESCRIPTION OF EMBODIMENTS OF THE INVENTION

Figure 1:
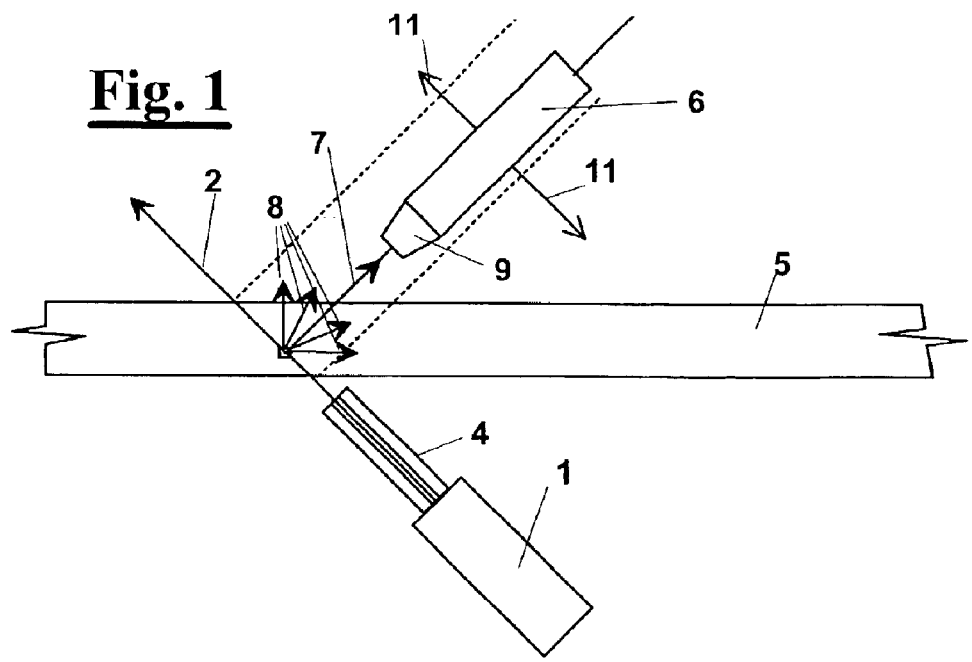
FIG. 1 illustrates one embodiment of the invention for continuously measuring the density profile of a panel.

For the purpose of promoting an understanding of the present invention, references will be made in the text hereof to embodiments of a non-destructive method and apparatus for continuously measuring the density profile of panels, only some of which are depicted in the drawings. It is nevertheless understood that no limitations to the scope of the invention are thereby intended. One of ordinary skill in the art will readily appreciate that modifications do not depart from the spirit and scope of the present invention, some of which are mentioned in the following description. In the embodiments depicted, like reference numerals refer to identical structural elements in the various drawings.

Figure 2:
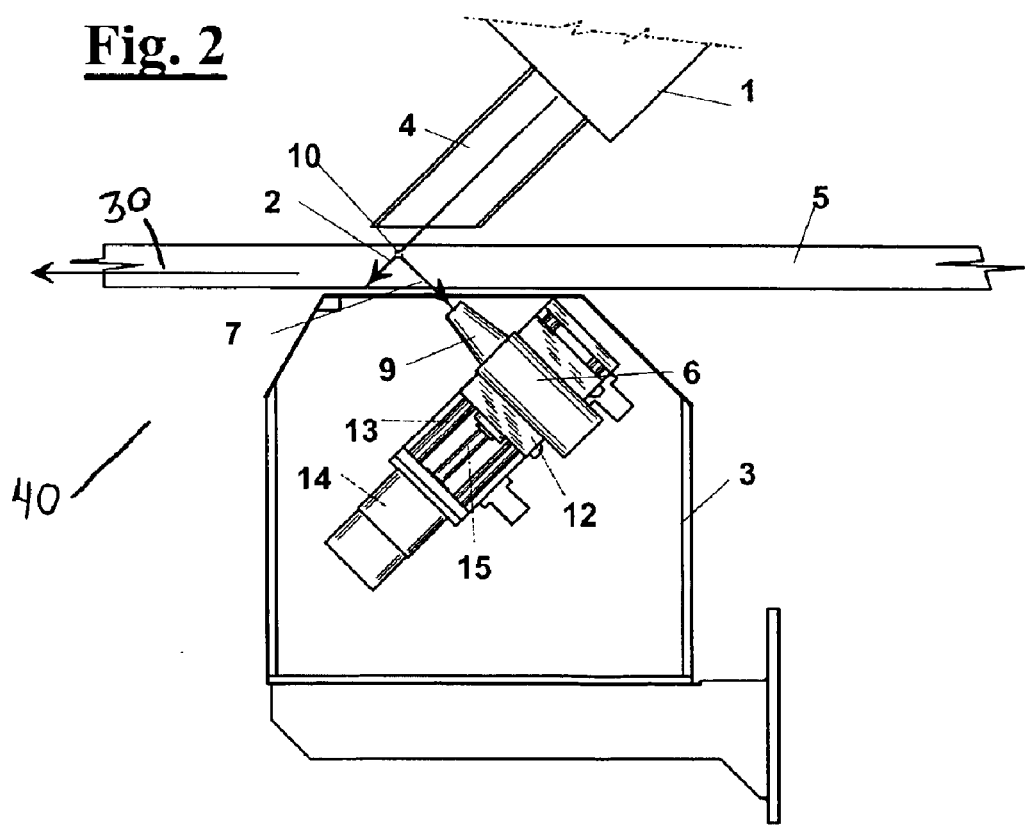
FIG. 2 depicts a more detailed illustration of the embodiment of the apparatus shown in FIG. 1.

FIG. 1 shows apparatus 40 for measuring the density profile of a wooden panel at the exit of a press (now shown); a density profile being a measure of the variation of the density over the thickness of an object being analyzed. Arrow 30 indicates the direction panel 5 passes as it exits the press. X-ray tube 1 is obliquely situated relative to panel 5 and is the X-radiation source which emits primary radiation beam 2 through first collimator 4. X-ray tube 1 contains a source of X-radiation commonly known in the art and includes a housing which absorbs all the radiation emitted by the source except radiation directed in one specific direction. X-ray tube 1 is placed adjacent to the side of panel 5 which can be the bottom side, as shown in FIG. 1, or the top side, as shown in FIG. 2. In one embodiment, X-ray tube 1 is situated at a 45° (forty five degree) angle from the horizontal plane of panel 5. At the opposite side of panel 5, X-ray detector 6 is provided. One of ordinary skill in the art will readily appreciate that other types of radiation, such as γ (gamma) radiation, can be used as primary radiation beam 2. Likewise, detector 6 can be a different type detector, such as a γ-ray detector, depending on the type of radiation used for primary radiation beam 2. Moreover, one of ordinary skill in the art will readily appreciate that panel 5 may be alternate media other than wood, such as plastic.

Primary radiation beam 2 interacts with panel 5 and partially passes through the material of panel 5 with photon-material interaction according to the Compton scattering effect. The number of photons scattered per second at a particular point is directly proportional to the density of panel 5 at that point. The interaction modifies primary beam 2, but does not alter the panel macroscopically. Therefore, this analysis is considered a nondestructive analysis.

As shown in FIG. 1, due to the Compton scattering effect, a plurality of resultant beams 8 are generated, which scatter in all directions. Second collimator 9 is provided to allow only the narrow beam of those X-rays scattered in a specific direction by Compton scattering to enter detector 6, such that only one resultant beam 7 is measured. In one embodiment, second collimator 9 and detector 6 are arranged at approximately a 45° angle relative to and on the opposite side of panel 5 such that second collimator 9 and detector 6 are at approximately a 90° angle with respect to X-ray tube 1 and first collimator 4, measuring only those resultant X-rays that are scattered at approximately a 90° angle relative to primary radiation beam 2. However, one of ordinary skill in the art will readily appreciate that the angle of second collimator 9 and detector 6 may be at another angle. Moreover, in an alternate embodiment, detector 6 is on the same side as X-ray tube 1 and collimator 4, but still at approximately a 90° angle relative to primary radiation beam 2. As shown by arrows 11 in FIG. 1, to scan the density of panel 5 throughout its thickness and to trace a curve proportional to the density profile, detector 6 can move laterally to detect resultant beam 7 at various depths within the thickness of panel 5.

That panel 5 is moving allows its density to be measured at the same depth in the material and, therefore, with a substantially constant density. However, the density profile of interest is that detected for the entire depth of the material and, for successive portions of panel 5, ensuring that the density profile is substantially equal. In fact, the density profile should change only by changing the production parameters of panel 5. Therefore, the fact that panel 5 is moving will hereinafter not be discussed.

FIG. 2 shows a more detailed version of the embodiment of X-ray detector 6 shown in FIG. 1. In this embodiment, the mechanical part on which detector 6 is present is mounted on base frame 3 and consists of carriage 12 driven on guide 13 by motor 14 by means of screw 15. Motor 14 moves carriage 12 according to a predetermined speed function and the pulses transmitted by detector 6 are responsive to the instant position of motor 14. On carriage 12, detector 6 is arranged with second collimator 9. Each time a density profile is measured, motor 14 moves for the whole stroke of carriage 12.

Figure 3:
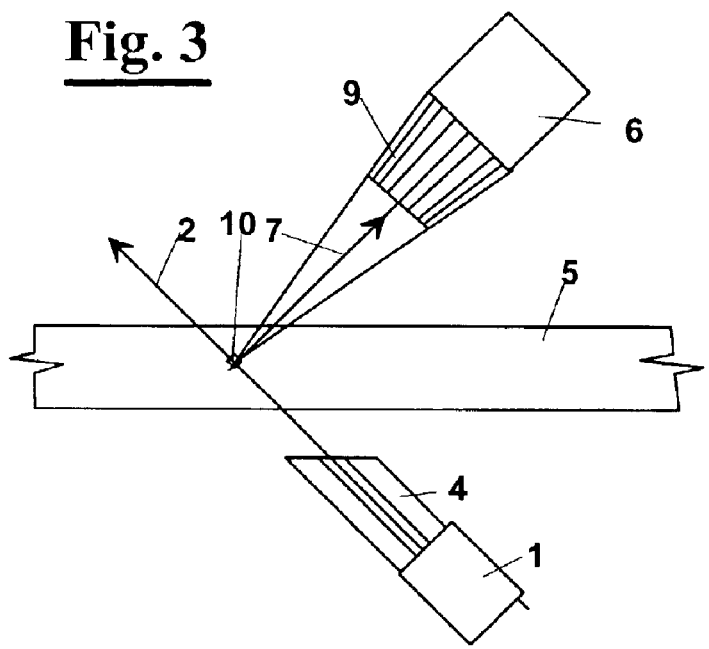
FIG. 3 illustrates the collimation of the radiation scattered by a particle within the panel being measured.

FIG. 3 shows that only one resultant beam 7 is measured by detector 6 by allowing only those photons produced under the Compton effect by the very tiny volume 10 of panel 5 being inspected. Second collimator 9, in the embodiment shown, has the shape of a pyramidal frustum. However, one of ordinary skill in the art will readily appreciate that collimator 9 may have alternate shapes, including but not limited to, conical. In addition, second collimator 9, in this embodiment, has steel blades of appropriate thickness and number to eliminate all resultant beams 8 except for resultant beam 7. Furthermore, any collimator readily available on the market may be used that allows only resultant beam 7 to be detected by detector 6 and measured.

Figure 4:
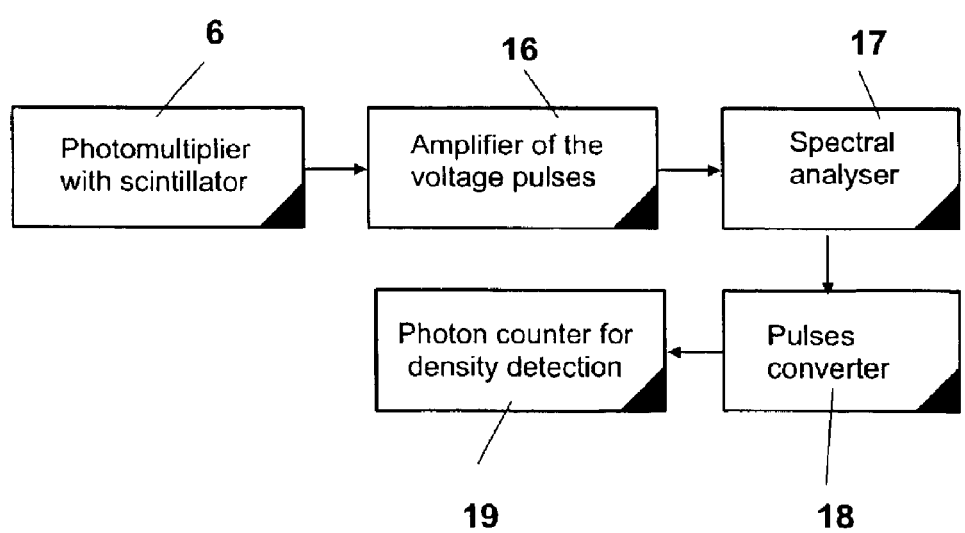
FIG. 4 shows a block diagram of the process by which an X-radiation photon is counted.

FIG. 4 shows a block diagram of the process by which an X-radiation photon is counted. Detector 6 is a photomultiplier with scintillator and has an output signal of a pulsed type. Using this configuration, a pulsed signal can be obtained for each photon received by the detector. The voltage amplitude of the output pulse depends on the energy of the photon. In fact, the scintillator produces a number of light photons responsive to the energy of the photon. These light photons are captured by the photocathode of the photomultiplier of detector 6. The light photons are converted into electrons and, with an avalanche effect between the stages that are polarized with a high voltage, a voltage pulse is produced. This voltage pulse is therefore dependent on the energy of the photon detected. Suitable scintillation detectors are produced by Scionix or by Crismatec Saint-Gobain. One of ordinary skill in the art will readily recognize, however, that this process is equally applicable to γ-radiation.

Figure 5:
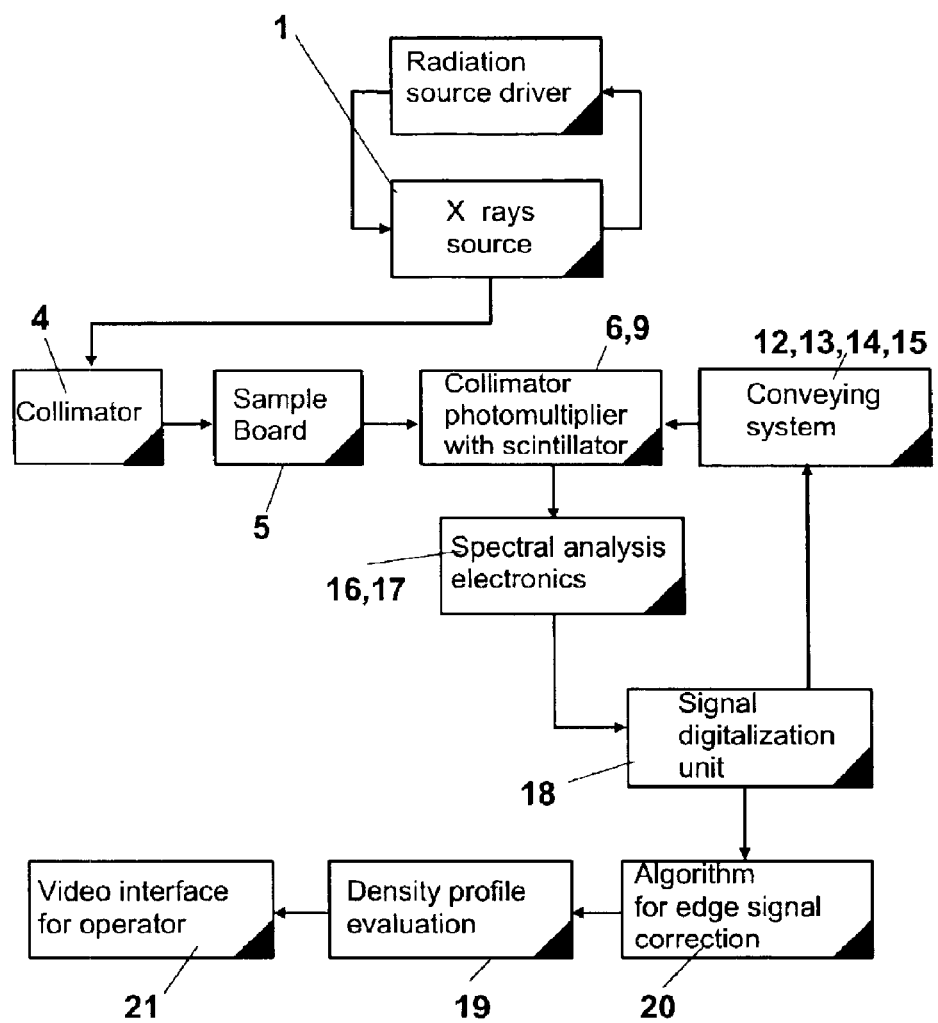
FIG. 5 is a block diagram of the method for analyzing the scattered radiation for computing the density profile.

With reference to the block diagrams of FIG. 4 and FIG. 5, where the whole apparatus is diagrammatically shown, in step 16, the pulsed signal is then amplified. Then, spectral analysis step 17 of the signal received by detector 6 is effected, selecting only the photons with energy within a particular range. This selection is made by a pulse converter 18 that chooses only those with a particular peak value. In this way, after the interaction under Compton effect, only the photons with a single energy are treated and, therefore, statistically the photons detected have immediately a same attenuation owing to is the mass absorption coefficient. The other signals are automatically excluded from the analysis. The voltage signal is proportional to the energy of the photons thus formed and is shaped as a series of pulses that can be counted at step 19. The number of pulses counted corresponds to the number of photons detected, which are directly proportional to the density of particle 10 examined.

Figure 6:
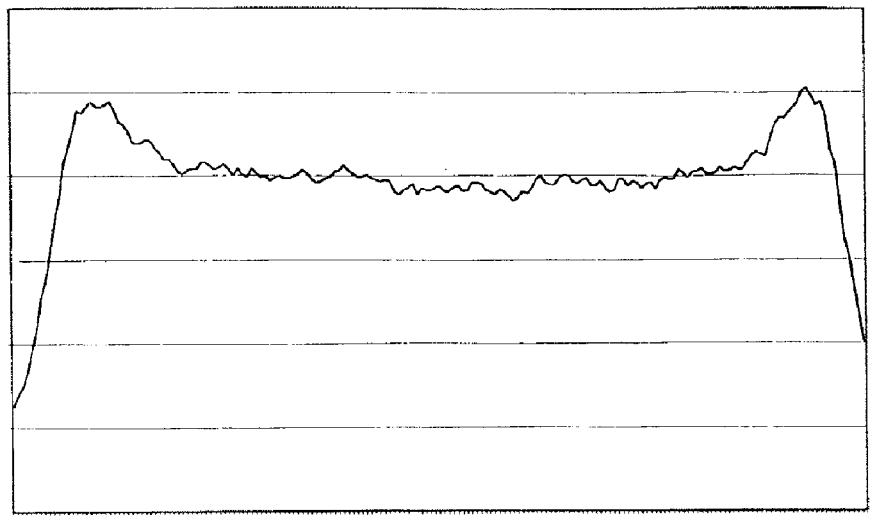
FIG. 6 shows an example density profile obtained by measuring the density a panel.

The pulses are of the same value of amplitude in voltage, about several Volts, whereas the number of pulses is directly proportional to the density of the panel. As a result, a series of values is created for each step of the motor along the thickness of panel 5. A system of correction, described infra, calculates the density at the side edges of panel 5 based on these values. All these points, if displayed graphically, provide a density profile. An example of such a density profile is shown in FIG. 6. Alternatively, the density of the sample being measured can be printed out or monitored by a computer, notifying the operator of any values outside of acceptable parameters.

Figure 7:
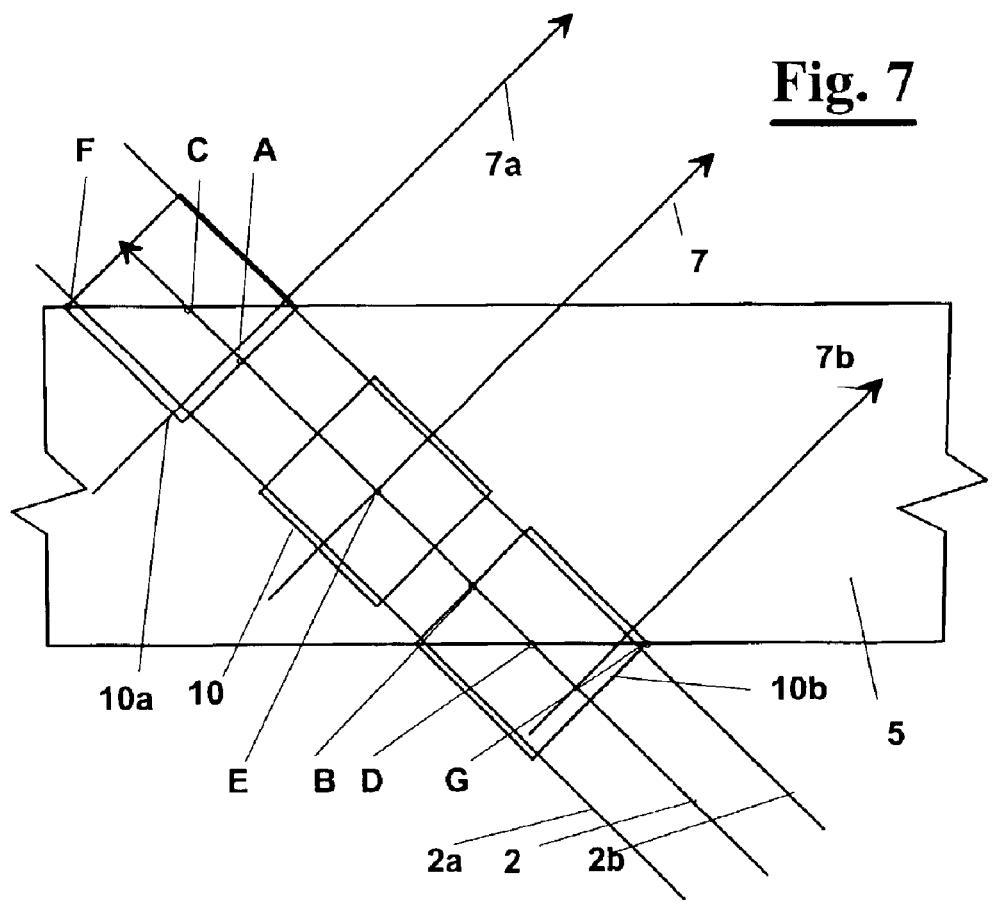
FIG. 7 shows a geometric view of the need to correct the density profile at the edges of the panel.

It must be noted that without any correction, by analyzing the signal for the whole thickness of panel 5, the result would be that the generated profile would only be accurate for the central part, and would be significantly in error for the values taken at the edges of panel 5. This can be overcome with geometrical considerations. As shown in FIG. 7, the second collimator (not shown) measures resultant beam 7, which is, in particular, a thin radiation beam of very small width. However, even if the collimation is precise, resultant beam 7 has a width not negligible with respect to the very small size of the photons detected. Therefore, the real thickness of primary radiation beam 2 must be considered. As shown in FIG. 7, where the size of primary radiation beam 2 has been exaggerated, it is shown that the detector (not shown) does not detect only the infinitesimal volume around examined point E, but also volume 10 depending on the thickness of primary radiation beam 2 and upon the angle of the first collimator (not shown). The differences examined are not very relevant in the central part of the panel, i.e. between examined points A and B, since volume 10, even if larger, is always fixed. However, when approaching the edges of panel 5, volume 10 examined decreases, reaching triangular shapes 10a and 10b at points C and D, respectively. Consequently, signals 7a and 7b, which are received by the detector and correspond to an attenuation near the edges, provide an inaccurate density profile.

Figure 8:
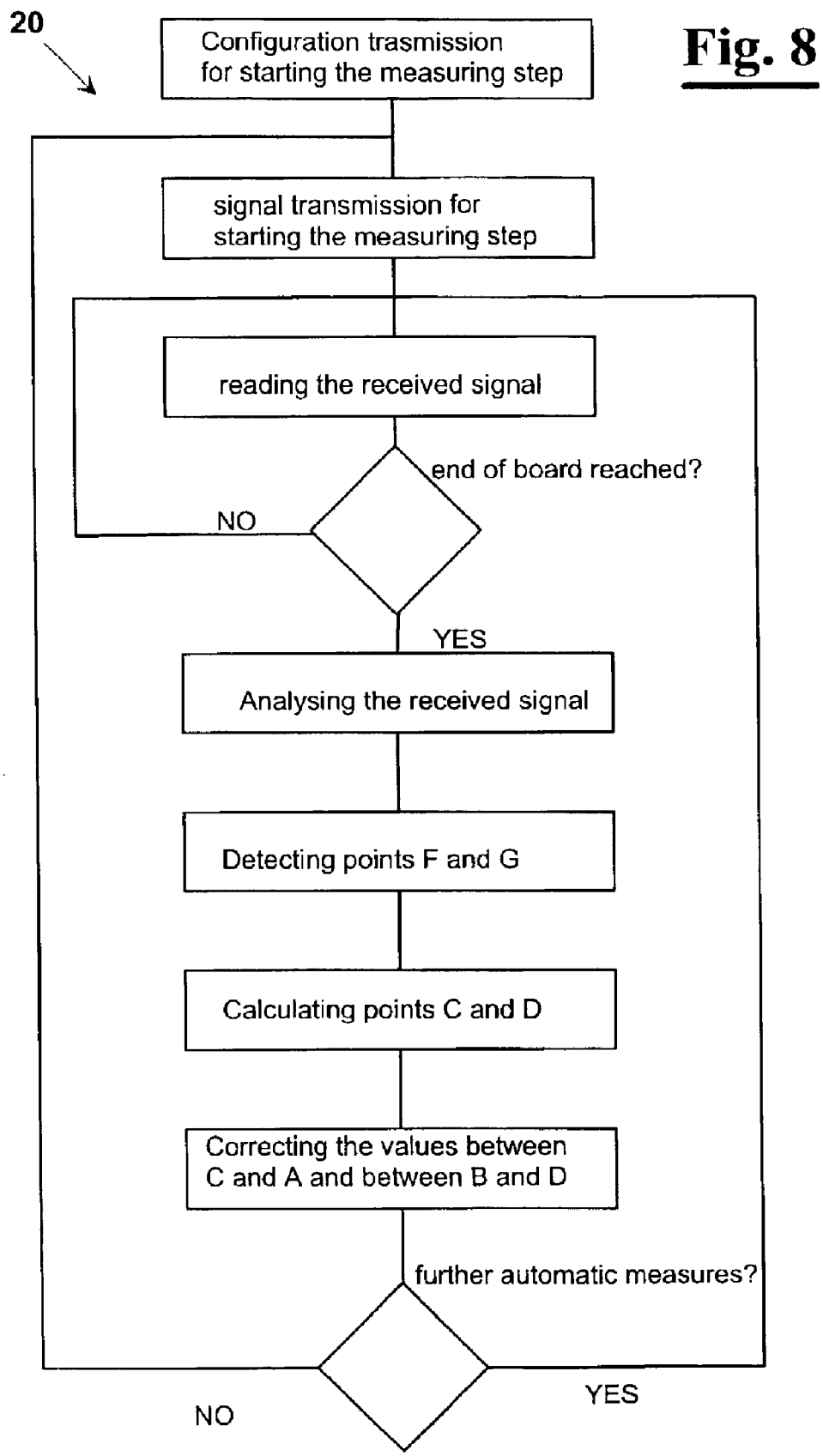
FIG. 8 is a flow chart of an algorithm for correction of the density measurement at the side edges of a panel.

To correct for the error at the edges, an algorithm is used. The algorithm is computed by block 20 of FIG. 5 and indicated in more detail in FIG. 8. The algorithm acquires the detected profile and corrects for edge inaccuracies taking into account the thickness of the panel, the size of the X-ray beam in different points of the panel, the focus of the collimator, and the non-linearity of the decrease of the volume occupied by the panel. Block 20 recognizes the curve of the detected profile and carries out the correction at the edges considering parameters that depend upon the dimensions of the beam and the collimator, easily determined by one of ordinary skill in the art. The algorithm automatically determines the point where the panel starts and the point where the signal coming from the panel ends. The algorithm of FIG. 8 outlines the real density profile along line 2. Primary radiation beam 2, however, has a real size, the width of which is exaggeratedly defined by lines 2a and 2b. The profile that has to be outlined must then be from point C to point D. Detector 6 starts measuring a signal other than zero at point F up to point G. In operation, the signal rises from point F to point A, follows the real trend of the density profile between points A and B, and undergoes a decrease from point B to point G. Then, the task of the algorithm is to determine the above points (A, B, C, D, F, G) and to make a correction starting at point C and up to point A in order to compensate for the lack of signal at the end of the sample. The same is done for between points B and D.

Reference has been made only to the use of detector 6. According to the principles of the invention, alternate detectors can be employed, or detector 6 can be on the other side of panel 5, or at different angles. Furthermore, in an alternate embodiment, one or more of the spectral analyzer, the attenuation compensation means, and the software for correcting inaccuracies near the side edges of the panel being analyzed can be contained within an electronic control unit.

Furthermore, notwithstanding the step of counting the pulses as elaborated after spectral analysis is made based on voltage signals that have been directly transformed into digital signals and discriminated according to their shape, this does not exclude that the voltage signals can be determined as analog signals, filtered, and then converted into digital signals.

The preceding description of a specific embodiment should so fully reveal and explain the invention that others, by applying current knowledge, will be able to modify and/or adapt for various applications such an embodiment without further research and without parting from the spirit and scope of the invention, and it is therefore to be understood that such adaptations and modifications will be considered equivalent to the specific embodiment. The means and the materials to realize the different functions described herein could have a different nature without, for this reason, departing from the field of the invention. It is to be understood that the phraseology or terminology employed herein is for the purpose of description and not of limitation.

What is claimed is:

1. A method for nondestructively measuring a density of a panel, comprising the steps of:
   directing a collimated radiation beam onto and along a length of said panel at a first oblique angle;
   continuously detecting a resultant beam of a plurality of emitted photons with at least one detector in a row directed at said panel and each of said at least one detector set at a second oblique angle;
   counting only photons of said plurality of emitted photons with an energy above a minimum energy level, wherein said counting step is performed by each of said at least one detector, each of said at least one detector comprised of:
      a scintillation detector, said scintillation detector comprised of a crystal and a photomultiplier tube, said crystal producing a plurality of light photons when an X-ray or gamma ray is detected, and said photomultiplier tube amplifying said plurality of light photons and converting said plurality of light photons into a pulse of electrons;
      a spectral analyzer comprised of a discriminator, said discriminator selecting only light photons of said plurality of light photons with an energy level above said minimum energy level, a pulse converter, said pulse converter converting said pulse of electrons into at least one digital signal, and a counter, said counter counting said at least one digital signal; and
      supporting electronics, said supporting electronics electronically connecting said scintillation detector and said spectral analyzer; and
   generating a density profile of said panel.

2. The method of claim 1, wherein said method further includes a correcting step for correcting for inaccuracies at at least one edge of said panel, said correcting step using an algorithm which takes into account a thickness of said collimated radiation beam, said first oblique angle, and a geometry of said at least one edge of said panel.

3. The method of claim 1, wherein said panel is selected from a group comprised of wood and plastic.

4. The method of claim 1, wherein said collimated radiation beam is selected from a group comprising X-rays and gamma rays.

5. The method of claim 1, wherein said collimated radiation beam is emitted from an X-ray tube with a first collimator, wherein said X-ray tube is comprised of a housing and a radiation source contained within said housing, said housing being configured to absorb substantially all radiation of said radiation source except a narrow radiation beam, said narrow radiation beam being further collimated by said first collimator to produce said collimated radiation beam.

6. The method of claim 1, wherein said first oblique angle is approximately 45° relative to a surface of said panel.

7. The method of claim 1, wherein said second oblique angle is approximately 45° relative to a surface of said panel.

8. The method of claim 1, wherein each of said at least one detector is situated at approximately a 90° angle relative to said collimated radiation beam.

9. The method of claim 5, wherein said first collimator and said at least one detector are formed as one integral unit.

10. The method of claim 5, wherein said at least one detector is on an opposite side of said panel as said X-ray tube and said first collimator.

11. The method of claim 1, wherein each of said at least one detector further includes a second collimator to permit only said resultant beam of a plurality of emitted photons coming from a specific direction to enter each of said at least one detector.

12. The method of claim 1, wherein said directing said collimated radiation beam along said length of said panel step is completed by moving said collimated radiation beam along said length of said panel.

13. The method of claim 1, wherein said directing a collimated radiation beam step is completed by passing said panel under said collimated radiation beam.

14. The method of claim 2, wherein said directing step, said detecting step, said counting step, said correcting step, and said generating step are repeated at least one additional time, wherein each of said at least one detector is directed at said panel at a third oblique angle to produce a second density profile of said panel at a second depth of said panel.

15. The method of claim 14, wherein each of said at least one detector further includes:
   a guide;
   a carriage mounted on said guide; and
   a motor and a screw for driving said carriage according to a predetermined speed function and for providing a lateral movement to each of said at least one detector so that said panel can be measured at a plurality of depths of said panel.

16. A nondestructive method for measuring the density of a panel, comprising the steps of:
   directing a collimated radiation beam at said panel at a first oblique angle and along a length of said panel;
   continuously detecting a resultant beam of a plurality of emitted photons with at least one detector in a row, said at least one detector directed at said panel and each of said at least one detector being set at a second oblique angle;
   counting only photons of said plurality of emitted photons with an energy above a minimum energy level, wherein said counting step is performed by said at least one detector, each of said at least one detector being comprised of:
      a scintillation detector, said scintillation detector comprised of a crystal and a photomultiplier tube, said crystal producing a plurality of light photons when an X-ray or gamma ray is detected, and said photomultiplier tube amplifying said plurality of light photons and converting said plurality of light photons into a pulse of electrons;

a spectral analyzer comprised of a discriminator, a pulse converter, and a counter, said discriminator selecting only light photons of said plurality of light photons with an energy level above said minimum energy level, said pulse converter converting said pulse of electrons into a digital signal, and said counter counting said digital signal; and supporting electronics, said supporting electronics electronically connecting said scintillation detector and said spectral analyzer;

repeating said directing step, said detecting step, and said counting step at least one additional time along said length of said panel; and generating a density profile of said panel.

17. The method of claim 16, wherein said method further includes a correcting step for correcting for inaccuracies at at least one edge of said panel, wherein said correcting step uses an algorithm which considers a thickness of said collimated radiation beam, said first oblique angle, and a geometry of said at least one edge of said panel.

18. The method of claim 16, wherein said panel is selected from a group comprised of wood and plastic.

19. The method of claim 16, wherein said collimated radiation beam is selected from a group comprising X-rays and gamma rays.

20. The method of claim 16, wherein said collimated radiation beam is emitted from an X-ray tube with a first collimator, wherein said X-ray tube is comprised of a housing and a radiation source contained within said housing, said housing being configured to absorb substantially all radiation of said radiation source except a narrow radiation beam, said narrow radiation beam being further collimated by said first collimator to produce said collimated radiation beam.

21. The method of claim 16, wherein said first oblique angle is approximately 45°, relative to a surface of said panel.

22. The method of claim 16, wherein said second oblique angle is approximately 45°, relative to a surface of said panel.

23. The method of claim 20, wherein each of said at least one detector is situated at approximately a 90° angle relative to said collimated radiation beam and is on an opposite side of said panel as said X-ray tube and said first collimator.

24. The method of claim 20, wherein said first collimator and each of said at least one detector are formed as one integral unit.

25. The method of claim 16, wherein each of said at least one detector further includes a second collimator to allow only said resultant beam of a plurality of emitted photons coming from a specific direction to enter each of said at least one detector.

26. The method of claim 16, wherein said directing a collimated radiation beam along a length of said panel step is completed by moving said collimated radiation beam along said length of said panel.

27. The method of claim 16, wherein said directing a collimated radiation beam step is completed by passing said panel under said collimated radiation beam.

28. The method of claim 16, wherein each of said at least one detector further includes:

a guide;

a carriage mounted on said guide; and a motor and a screw for driving said carriage according to a predetermined speed function and for providing a lateral movement to each of said at least one detector so that said panel can be measured at a plurality of depths of said panel.

29. An apparatus for continuously measuring a density profile of a panel comprising:

a radiation source, said radiation source emitting a plurality of radiation beams;

a device for collimating said plurality of radiation beams into a collimated radiation beam towards said panel and oriented at a first oblique angle with respect to a first side of said panel and along a length of said panel;

at least one detector in a row for detecting a resultant beam scattered under Compton effect by a particle of said panel, each of said at least one detector oriented at a second oblique angle with respect to said panel and converting said resultant beam to a plurality of pulsed electron signals, counting only those pulsed electron signals of said plurality of pulsed electron signals within a predetermined energy range, producing a density profile of said panel based on said plurality of said pulsed electron signals within said predetermined energy range, and being arranged at a predetermined inclination with respect to said device for collimating;

an algorithm for correcting said density profile of said panel at at least one edge of said panel, said algorithm taking into account factors from a group comprising a thickness of said collimated radiation beam, said first oblique angle, and a geometry of said at least one edge of said panel; and a mechanism for moving each of said at least one detector so that each of a plurality of successive depths of said panel can be measured.

30. The apparatus of claim 29, wherein said panel is selected from a group comprised of wood and plastic.

31. The apparatus of claim 29, wherein said radiation source emits said plurality of radiation beams selected from a group comprising X-rays and gamma rays.

32. The apparatus of claim 29, wherein said device for collimating said plurality of radiation beams is further comprised of an X-ray tube with a first collimator, wherein said X-ray tube is comprised of a housing substantially enclosing said radiation source, said housing being configured to absorb substantially all of said plurality of radiation beams of said radiation source except a narrow radiation beam, said narrow radiation beam being further collimated by said first collimator to produce said collimated radiation beam.

33. The apparatus of claim 29, wherein said device for collimating said plurality of radiation beams is oriented at approximately a 45° angle relative to said first side of said panel.

34. The apparatus of claim 29, wherein said predetermined inclination of each of said at least one detector for detecting said resultant beam is oriented at approximately a 45° angle relative to said panel.

35. The apparatus of claim 29, wherein each of said at least one detector is for detecting a resultant beam is at approximately a 90° angle relative to said device for collimating said plurality of radiation beams.

36. The apparatus of claim 32, wherein said first collimator and said at least one detector are formed as one integral unit.

37. The apparatus of claim 29, wherein each of said at least one detector for detecting a resultant beam is on an opposite side of said panel as said device for collimating said plurality of radiation beams.

38. The apparatus of claim 29, wherein said density profile is completed by moving said apparatus along said length of said panel.

39. The apparatus of claim 29, wherein said density profile is completed by passing said panel under said apparatus.

40. The apparatus of claim 29, wherein each of said at least one detector includes:
- a scintillation detector, said scintillation detector further comprised of a crystal and a photomultiplier tube, said crystal producing a plurality of light photons when an X-ray or gamma ray is detected, and said photomultiplier tube amplifying said plurality of light photons and converting said plurality of light photons into said plurality of pulsed electron signals;
- a spectral analyzer comprised of a discriminator, said discriminator selecting only said pulsed electron signals of said plurality of pulsed electron signals within said predetermined energy range, a pulse converter, said pulse converter converting said pulsed electron signals into a digital signal, and a counter, said counter counting said digital signal; and
- supporting electronics, said supporting electronics electronically connecting said scintillation detector and said spectral analyzer.

41. The apparatus of claim 29, wherein each of said at least one detector for detecting a resultant beam further includes a second collimator to permit only photons coming from a specific direction to enter said at least one detector.

42. The apparatus of claim 29, wherein mechanism for moving said at least one detector further includes:
- a guide;
- a carriage mounted on said guide; and
- a motor and a screw for driving said carriage according to a predetermined speed function and for providing a lateral movement to each of said at least one detector so that said panel can be measured at a plurality of depths of said panel.

* * * * *

UNITED STATES PATENT AND TRADEMARK OFFICE
CERTIFICATE OF CORRECTION

PATENT NO. : 6,895,074 B2
DATED : May 17, 2005
INVENTOR(S) : Paolo Benedetti

It is certified that error appears in the above-identified patent and that said Letters Patent is hereby corrected as shown below:

Column 1,
Line 25, "coefficient, A," should read -- coefficient, $\mu$, --.

Column 5,
Line 59, "is" should be deleted.

Signed and Sealed this

Twenty-eighth Day of June, 2005

JON W. DUDAS
*Director of the United States Patent and Trademark Office*